US006638310B2

(12) United States Patent
Lin et al.

(10) Patent No.: US 6,638,310 B2
(45) Date of Patent: Oct. 28, 2003

(54) INTERVERTEBRAL SPACER AND IMPLANT INSERTION INSTRUMENTATION

(75) Inventors: Jo-Wen Lin, Tinton Falls, NJ (US); Nelson L. Scarborough, Ocean, NJ (US); Lawrence Shimp, Morganville, NJ (US); David Kaes, Toms River, NJ (US)

(73) Assignee: Osteotech, Inc., Eatontown, NJ (US)

( * ) Notice: Subject to any disclaimer, the term of this patent is extended or adjusted under 35 U.S.C. 154(b) by 159 days.

(21) Appl. No.: 09/734,860

(22) Filed: Dec. 12, 2000

(65) Prior Publication Data

US 2002/0016633 A1 Feb. 7, 2002

Related U.S. Application Data

(60) Provisional application No. 60/220,941, filed on Jul. 26, 2000.

(51) Int. Cl.[7] .................................................. A61F 2/44
(52) U.S. Cl. .................................. 623/17.11; 623/17.16
(58) Field of Search ............................. 623/16, 17, 18, 623/23, 17.11, 17.16

(56) References Cited

U.S. PATENT DOCUMENTS

| 4,484,570 A | 11/1984 | Sutter et al. |
| 4,516,276 A | 5/1985 | Mittelmeier et al. |
| 4,566,466 A | 1/1986 | Ripple et al. |

(List continued on next page.)

FOREIGN PATENT DOCUMENTS

| WO | 00/24327 | 5/2000 |
| WO | 00/40177 | 7/2000 |
| WO | 00/40179 | 7/2000 |

OTHER PUBLICATIONS

Sofamar Danek—Surgical Technique Using Bone Dowel Instrumentation for Anterior Approach [Publication Date Unknown].
University of Florida Tissue Bank, Inc., Allograft Catalog [Publication Date Unknown].

(List continued on next page.)

Primary Examiner—David J. Isabella
Assistant Examiner—Kamrin Landrem
(74) Attorney, Agent, or Firm—Dilworth & Barrese, LLP

(57) ABSTRACT

An intervertebral spacer formed of dense cancellous human or animal bone is provided. In one preferred embodiment, the intervertebral spacer includes at least one bore which is dimensioned to receive a plug formed from cortical bone tissue. The cortical bone plug provides increased mechanical strength to the intervertebral spacer. Instrumentation for gauging the size of an intervertebral receiving bed and for grasping and inserting an intervertebral spacer or implant into an intervertebral receiving bed are also provided. These instruments include a spacer trial or set of spacer trials for determining the appropriate size spacer required for a particular surgical procedure, a spacer introducer for grasping and positioning a spacer at least partially within a receiving bed formed in the intervertebral space, and a bone tamp for driving a spacer into the receiving bed. Any one or all of these instruments may be provided in a kit for inserting an implant into the intervertebral space. The kit may also include one or more intervertebral spacers or implants.

11 Claims, 7 Drawing Sheets

U.S. PATENT DOCUMENTS

| | | |
|---|---|---|
| 4,637,931 A | 1/1987 | Schmitz |
| 4,834,757 A | 5/1989 | Brantigan |
| 4,950,296 A * | 8/1990 | McIntyre .................... 606/76 |
| 4,961,740 A | 10/1990 | Ray et al. |
| 5,061,786 A | 10/1991 | Burnier et al. |
| 5,192,327 A | 3/1993 | Brantigan |
| 5,207,710 A | 5/1993 | Chu et al. |
| 5,298,254 A | 3/1994 | Prewett et al. |
| 5,314,476 A | 5/1994 | Prewett et al. |
| 5,423,817 A | 6/1995 | Lin |
| 5,439,684 A | 8/1995 | Prewett et al. |
| 5,443,514 A | 8/1995 | Steffee |
| 5,507,813 A | 4/1996 | Dowd et al. |
| 5,522,899 A | 6/1996 | Michelson |
| 5,545,222 A | 8/1996 | Bonutti |
| 5,607,424 A | 3/1997 | Tropiano |
| 5,609,636 A | 3/1997 | Kohrs et al. |
| 5,653,763 A | 8/1997 | Errico et al. |
| 5,662,710 A | 9/1997 | Bonutti |
| 5,709,683 A | 1/1998 | Bagby |
| 5,716,415 A | 2/1998 | Steffee |
| 5,728,159 A * | 3/1998 | Stroever et al. ........... 623/23.5 |
| 5,749,916 A | 5/1998 | Richelsoph |
| 5,769,897 A | 6/1998 | Härle |
| 5,776,199 A | 7/1998 | Michelson |
| 5,782,830 A | 7/1998 | Farris |
| 5,800,547 A | 9/1998 | Schäfer et al. |
| 5,814,084 A | 9/1998 | Grivas et al. |
| 5,824,078 A | 10/1998 | Nelson et al. |
| 5,868,749 A | 2/1999 | Reed |
| 5,888,219 A | 3/1999 | Bonutti |
| 5,888,222 A | 3/1999 | Coates |
| 5,899,939 A | 5/1999 | Boyce et al. |
| 5,968,047 A | 10/1999 | Reed |
| 5,984,967 A | 11/1999 | Zdeblick et al. |
| 5,989,289 A | 11/1999 | Coates |
| 6,030,635 A | 2/2000 | Gertzman et al. |
| 6,066,174 A | 5/2000 | Farris |
| 6,083,225 A | 7/2000 | Winslow et al. |
| 6,111,164 A | 8/2000 | Rainey et al. |
| 6,113,638 A | 9/2000 | Williams et al. |
| 6,132,472 A | 10/2000 | Bonutti |
| 6,159,215 A | 12/2000 | Urbahns et al. |
| 6,379,385 B1 * | 4/2002 | Kalas et al. ............. 623/16.11 |

OTHER PUBLICATIONS

University of Florida Tissue Transplant Patient Education Series [Publication Date Unknown].

Gerhart et al., J Orthop Res (1986); 4(1):86–85 —Biomechanical optimization of a model particulate composite for orthopaedic applications [Abstract Only].

Tan et al., A modified technique of anterior Lumbar fusion with femoral cortical allograft; J. Orthop Surg Tech; vol. 5, No. 3, (1990) pp. 83–93.

Frymoyer et al., Eds., The Adult Spine Principles and Practice, Poster Lumbar Interbody Fusion, James W. Simmons, vol. 2, pp. 1961–1987 (1991).

Ma, G.W.C., Posterior Lumbar Interbody Fusion with Specialized Instruments, Clinical Ortho and Rel Res, 193 (Mar) pp. 57–63 (1985).

Lewandrowski et al., Improved Osteoinduction of Cortical Bone Allografts: A Study of the Effects of Laser Perforation and Partial Demineralization, J Ortho Res 15: 748–756 (1997).

Stevenson, S., Enhancement of Fracture Healing With Autogenous and Allogeneic Bone Grafts, Clin Ortho Rel Res 355S, pp. S239–S246 (1998).

McCord et al., Anterior endoscopic thoracolumbar instrumentation and implants, Curr Ortho 12, pp. 96–103 (1998).

DePuy AcroMed, Lumbar I/F Cage Implants & Instruments (Product Catalog) (1999).

Brantigan, J.W., DePuy AcroMed, Lumbar I/F Cage With VSP Spinal System (Surgical Technique) (1999).

* cited by examiner

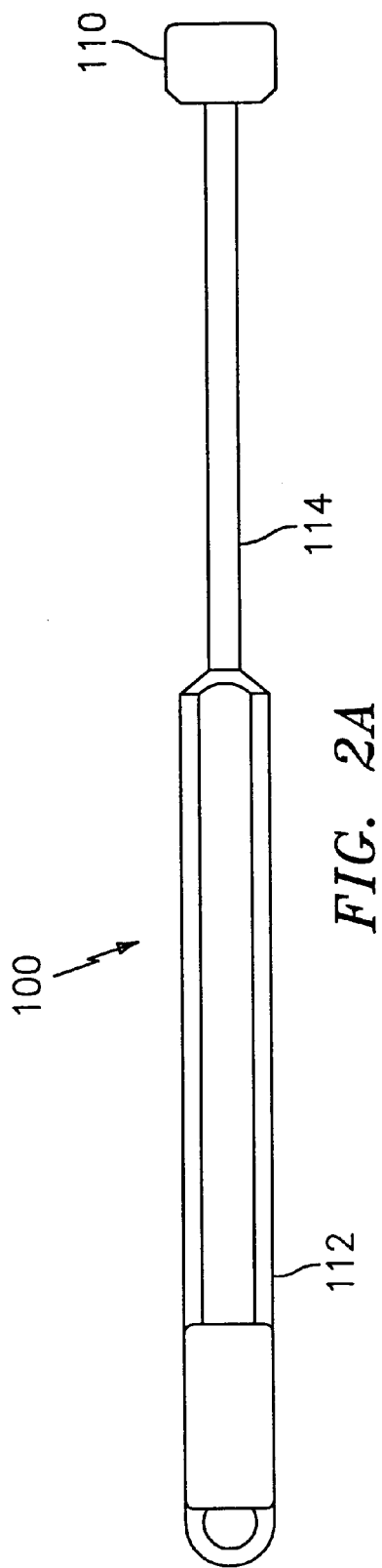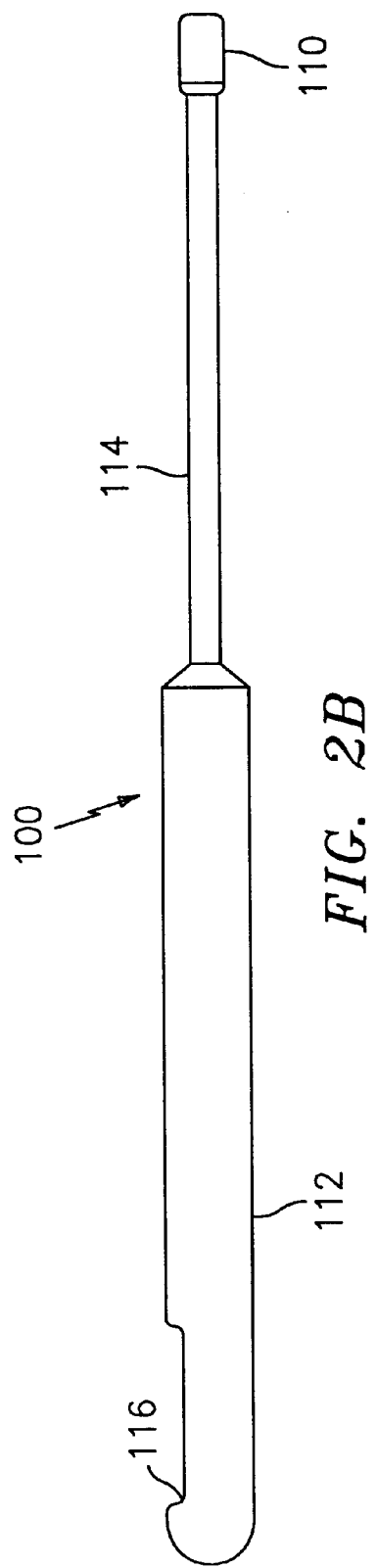

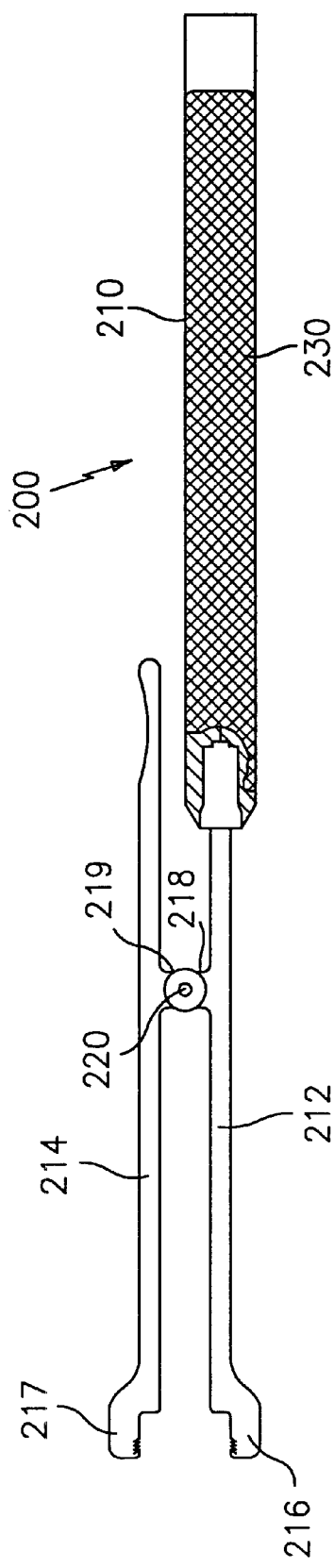
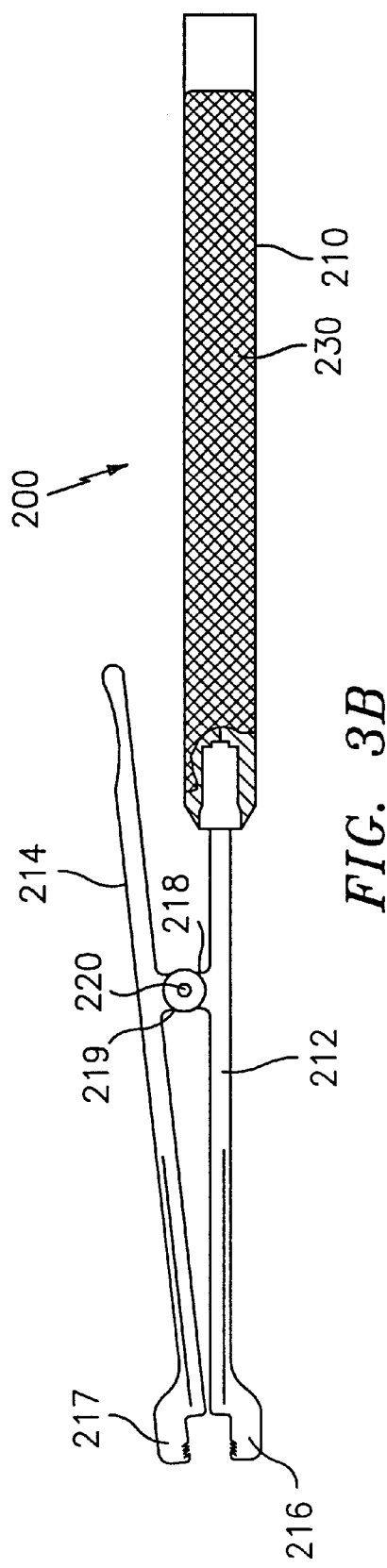

ical Field
INTERVERTEBRAL SPACER AND IMPLANT INSERTION INSTRUMENTATION

This application claims priority from U.S. provisional application Serial No. 60/220,941, filed Jul. 26, 2000, which is incorporated herein by reference.

BACKGROUND

1. Technical Field

The present disclosure relates generally to spinal implants and to spinal implant insertion instruments, and more particularly, to a spinal implant suitable for insertion into a receiving bed formed in the cervical region of the spine and to spinal implant insertion instruments adapted to facilitate the placement of an implant into a receiving bed formed in an intervertebral space.

2. Background of Related Art

Intervertebral implants for fusing together adjacent vertebrae of spinal column are well known in the art. Such implants are formed in a variety of different shapes and sizes and are configured for insertion into receiving beds formed in the various regions of the spine. Such implants are also formed of a variety of different biologically compatible materials including ceramics, polymers, human or animal bone, composites, etc. Intervertebral implants formed of natural bone may be formed of cancellous or cortical bone. Typically, due to its limited mechanical strength, implants constructed entirely from cancellous bone are used in the cervical region of the spine. In contrast, cortical bone has the mechanical strength suitable for use in any region of the spine. Because of its osteoinductive properties, it is more desirable to use a spinal implant constructed from cancellous bone where possible, than a spinal implant formed of cortical bone.

Instruments for positioning implants in a receiving bed formed between adjacent vertebrae are also well known. Such instruments include instruments for gauging the size of a receiving bed, instruments for grasping an implant and instruments for driving an implant into the receiving bed.

U.S. Pat. No. 4,566,466 discloses a surgical instrument for sizing a graft for insertion between distracted vertebral bodies. Each instrument includes a template head having a pair of spaced parallel flat surfaces separated by a predetermined distance. A handle is attached to the template head for grasping by a surgeon. A plurality of depth indicating lines are formed on the template head. In use, a surgeon inserts the template head of the instruments into a receiving bed formed between the distracted vertebral bodies to determine the size implant required for a spinal fusion procedure. The size of the required implant is determined when a template head fits snugly within the receiving bed.

U.S. Pat. No. 6,066,174 discloses an implant insertion device for gripping a surgical implant. The instrument includes a handle, a shaft having a proximal end attached to the handle, a pair of jaws attached to the shaft and a hollow sleeve slidably positioned over the jaws. The jaws are biased apart to a release position. The hollow sleeve is slidable over the jaws to urge the jaws from the release position to an approximated position in which the jaws are approximated to grip an implant. In order to slide the hollow sleeve over the jaws, a surgeon must grasp the handle with one hand and advance the hollow sleeve over the jaws with the other hand. Thereafter, the surgeon must apply constant pressure on the hollow sleeve to prevent the implant from falling from between the jaws.

Accordingly, a continuing need exists for a spinal implant having improved strength characteristics and osteoinductive properties. A continuing need also exists for implant insertion tools which can be operated by a surgeon using a single hand.

SUMMARY

In accordance with the present disclosure, an intervertebral spacer formed of dense cancellous human or animal bone is provided. The implant may have a rectangular configuration or, in the alternative, may assume any configuration to meet a particular surgical requirement. In one preferred embodiment, the intervertebral spacer includes at least one bore which is dimensioned to receive a plug formed from cortical bone tissue. The cortical bone plug provided increased mechanical strength to the intervertebral spacer.

Instrumentation for gauging the size of an intervertebral receiving bed and for grasping and inserting an intervertebral spacer or implant into an intervertebral receiving bed are also provided. These instruments include a spacer trial or set of spacer trials for determining the appropriate size spacer required for a particular surgical procedure, a spacer introducer for grasping and positioning a spacer at least partially within a receiving bed formed in the intervertebral space, and a bone tamp for driving a spacer into the receiving bed. Any one or all of these instruments may be provided in a kit for inserting an implant into the intervertebral space. The kit may also include one or more intervertebral spacers or implants.

BRIEF DESCRIPTION OF THE DRAWINGS:

Preferred embodiments of the presently disclosed intervertebral spacer and insertion instruments are described herein with reference to the drawings, wherein;

FIG. 2A is a top view of one embodiment of the presently disclosed spacer trial;

FIG. 2B is a side view of the spacer trial shown in FIG. 2A;

FIG. 3A is a side view of one embodiment of the presently disclosed spacer introducer with jaws in an open position;

FIG. 3B is a side view of the spacer introducer shown in FIG. 3A with the jaws in an approximated position;

DETAILED DESCRIPTION OF PREFERRED EMBODIMENTS

Figure 1:
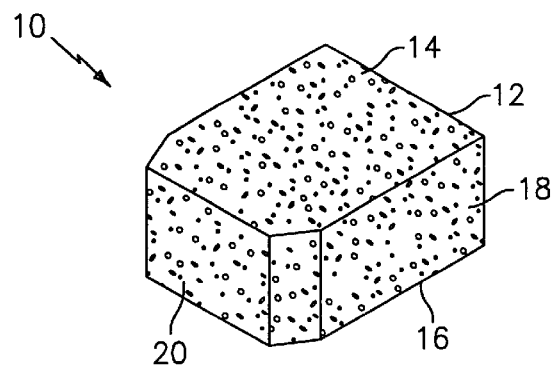
FIG. 1 is a perspective view of one preferred embodiment of the presently disclosed intervertebral spacer.

Preferred embodiments of the presently disclosed intervertebral spacer and implant insertion instruments will now be described in detail with reference to the drawings in which like reference numerals designate identical or corresponding elements in each of the several views.

Referring to FIG. 1, intervertebral spacer 10 includes a body 12 having a top 14, a bottom 16 and at least one sidewall 18. Body 12 is formed from dense cancellous human or animal bone which may be harvested from a bone such as a tibia, humerus, patella, calcaneus or femur. Body 12 may have a rectangular or square configuration and may be further configured to provide lordoses (not shown), i.e., top 14 and/or bottom 16 may be angled or shaped to maintain the natural curvature of the spine upon implantation. Alternately, body 12 may be formed to have other configurations including circular, hexagonal, etc. A trailing end 20 of spacer 10 includes a pair of angled walls 22.

Figure 1B:
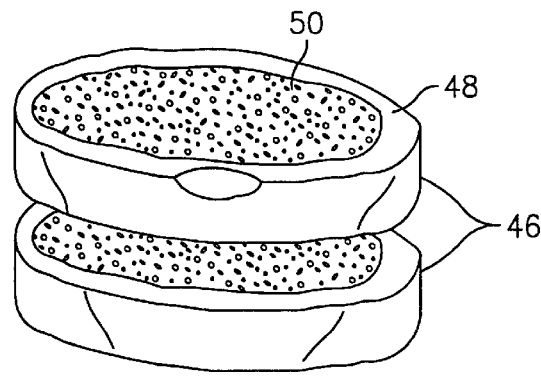
FIG. 1B is a perspective view of cut section taken from the long bone shown in FIG. 1A.
Figure 1A:
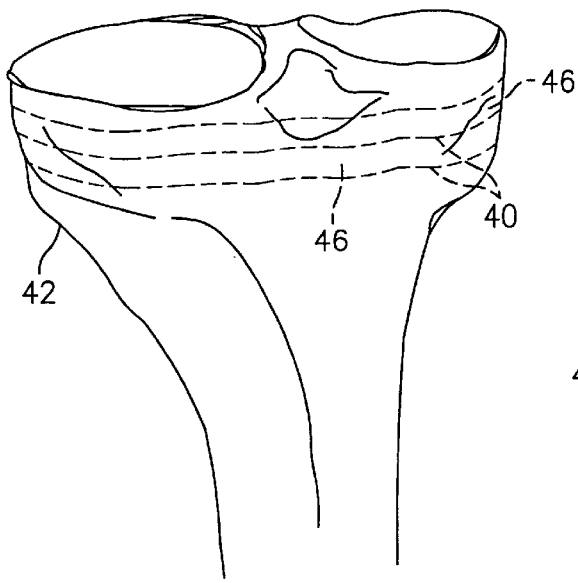
FIG. 1A is a perspective view of one end of a long bone from which the intervertebral spacer shown in FIG. 1 may be formed.
Figure 1C:
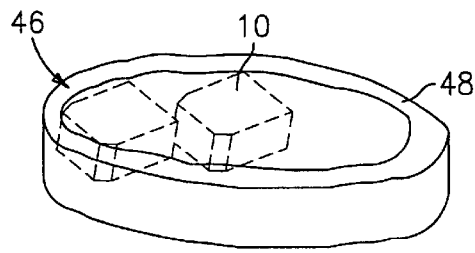
FIG. 1C is a perspective view of one of the cut sections shown in FIG. 1B with a pair of intervertebral spacers shown in phantom.

Referring to FIGS. 1A–1C, cervical spacer 10 (FIG. 1) may be formed by making horizontal cuts 40 in the metaphysics (subchondral layer) of a proximal tibia 42 (FIG. 1A) to form rings 46 (FIG. 1B). Each ring 46 includes an outer cortical shell 48 and an inner cancellous block plate 50. Cortical shell 48 can be removed from about cancellous block 50 and block 50 can be cut and/or shaped to form cervical spacer 10 (FIG. 1). By making horizontal cuts across the metaphysics of a long bone, cervical spacer 10 can be formed such that the loading on spacer 10, after spacer 10 has been implanted between adjacent vertebrae, will be in the same direction as was the anatomical loading on the bone.

FIGS. 2A and 2B illustrate the presently disclosed spacer trial shown generally as 100. Spacer trial 100 includes a head portion 110, a handle portion 112 and an elongated body portion 114 which interconnects head portion 110 and handle portion 112. Handle portion 112 includes a recess 116 to facilitate gripping. The flat surface defining the base of recess 116 may also be used for etching indicia, e.g., instrument name and size, manufacturer, etc. Preferably, spacer trial 100 is formed from a surgical grade metal such as stainless steel, e.g., 17-4 stainless steel. Alternately, trial 100 can be formed from any material suitable for surgical use and meeting the requisite strength requirements including plastics, metals, aluminum, etc. Head portion 112 has a predetermined shape and size which, preferably, corresponds to the shape and size of a spacer to be introduced into a receiving bed formed in the intervertebral space. Although only one spacer trial is shown, a set of spacer trials, each having a progressively larger size head portion, are provided. For example, a set of four trials may be provided each having a length of 11 mm and a width of 11 mm. The height of each trial increases by 1 mm from 5 mm to 8 mm. Alternately, nine trials may be provided, each trial having a head portion having a length of 11 mm, a width of 14 mm and a height which increases by 1 mm from 5 mm to 13 mm. Other trial head portion dimensions and set sizes are also envisioned.

In use, a surgeon will grasp handle portion 112 of a spacer trial 100 from a set of spacer trials (not shown) and position head portion 110 of spacer trial 100 into a receiving bed formed between adjacent vertebrae. The surgeon will repeat this process until the head portion of a spacer trial fits snugly within the receiving bed. Since each spacer trial includes a head portion which corresponds in size to a particular size spacer, the appropriate size spacer is identified when a spacer trial fits snugly within the receiving bed.

FIGS. 3A and 3B illustrate the presently disclosed spacer introducer shown generally as 200. Spacer introducer 200 includes a handle 210, a stationary arm 212, and a pivotable arm 214. Each arm has a proximal end and a distal end having a jaw 216 and 217, respectively, formed thereon. The proximal end of stationary arm 212 is fastened to handle 210 using any known fastening technique including welding, screw threads, adhesives, etc . . . Each arm 212 and 214 includes a centrally located transverse extension 218 and 219, respectively, adapted to receive a pivot member 220. Pivotable arm 214 is pivotably secured to stationary arm 212 about pivot member 220 such that jaws 216 and 217 can be moved between spaced (FIG. 3A) and approximated positions (FIG. 3B). A biasing member (not shown) is positioned between transverse extensions 218 and 219 to urge jaws 216 and 217 to the approximated position. Preferably, introducer 200 is formed from surgical grade steel, although other materials suitable for surgical use may also be used including plastics, metals, etc.

In use, a surgeon can grasp introducer 200 by handle 210, which may include a knurled or roughened outer surface 230 to improve gripping. Using his thumb, the surgeon can press on the proximal end of pivotable arm 214 to pivot jaw 217 away from jaw 216 to the spaced position. A spacer or implant can now be positioned between jaws 216 and 217. The surgeon can now release pivotable arm 214 to allow jaw 217 to be urged towards the approximated position by the biasing member to compress the trailing end of a spacer between the jaws. Each jaw 216 and 217 may include ridges 224 to prevent the spacer from slipping from between the jaws. The surgeon can now maneuver the introducer 200 to position the leading end of a spacer into a receiving bed formed between the adjacent vertebrae.

Figure 4A:
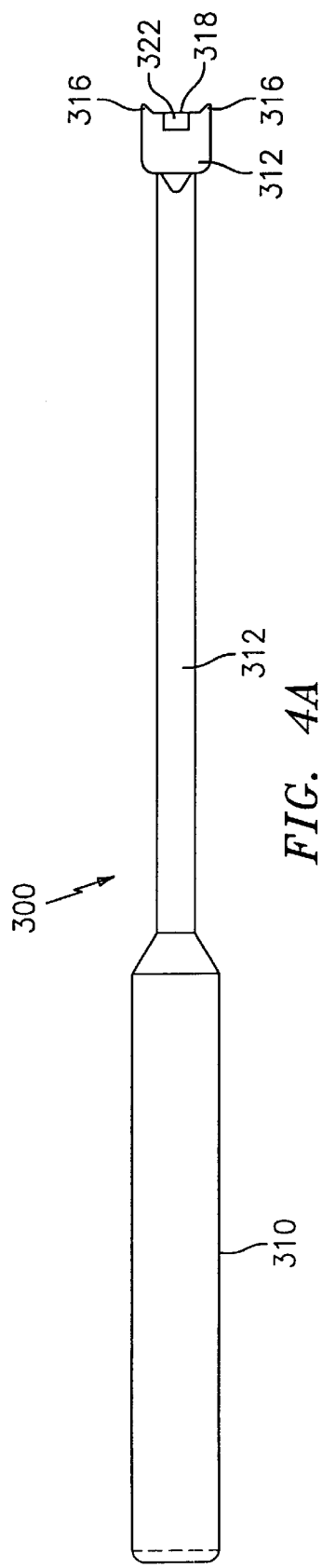
FIG. 4A is a top view of one embodiment of the presently disclosed bone tamp.
Figure 4B:
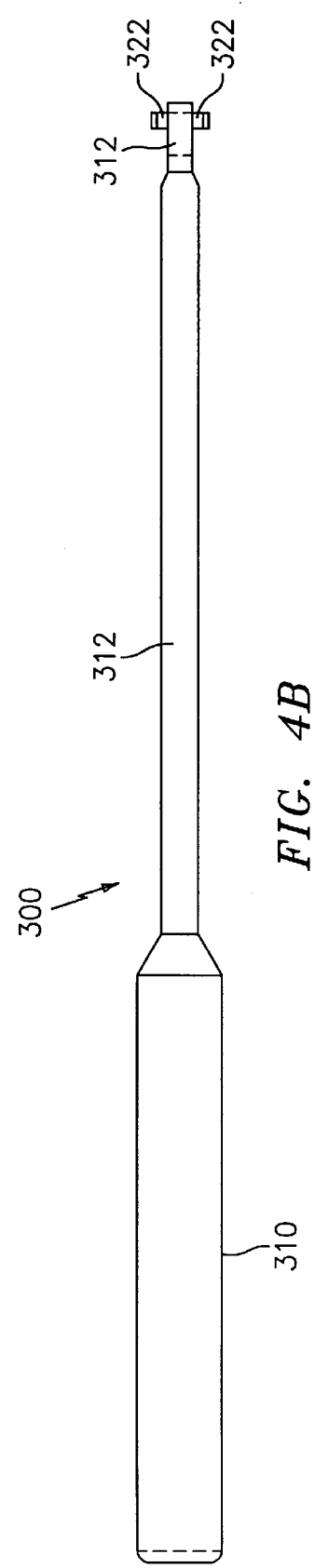
FIG. 4B is a side view of the bone tamp shown in FIG. 4A.

FIGS. 4A and 4B illustrate the presently disclosed bone tamp shown generally as 300. Bone tamp 300 includes a handle portion 310, a head portion 312 and an elongated body portion 314 interconnecting head portion 312 and handle portion 310. Head portion 312 includes a pair of spaced angled extensions 316 defining a recess 318. Recess 318 is configured to matingly engage trailing end 20 of spacer 10. A pair of depth limiting stops 322 extend upwardly and downwardly from head portion 312. Stops 322 are positioned to engage the adjacent vertebrae after a spacer has been driven into a receiving bed formed in the intervertebral space.

Figure 5:
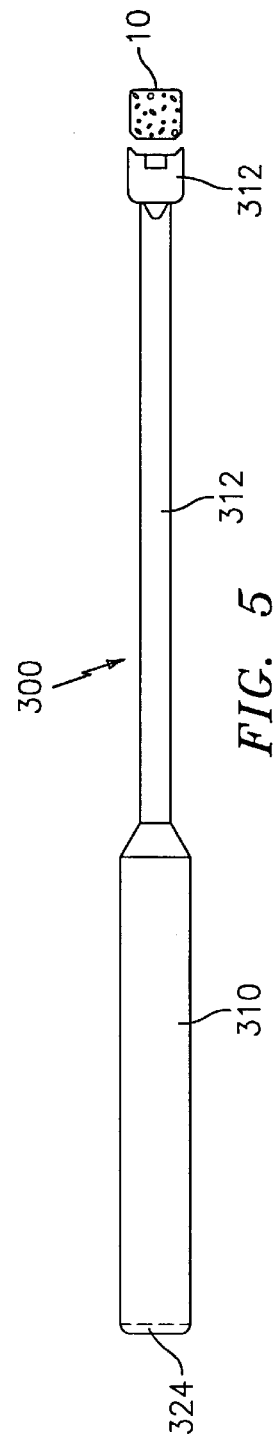
FIG. 5 is a top view of the presently disclosed bone tamp positioned to engage the intervertebral spacer shown in FIG. 1.
Figure 5A:
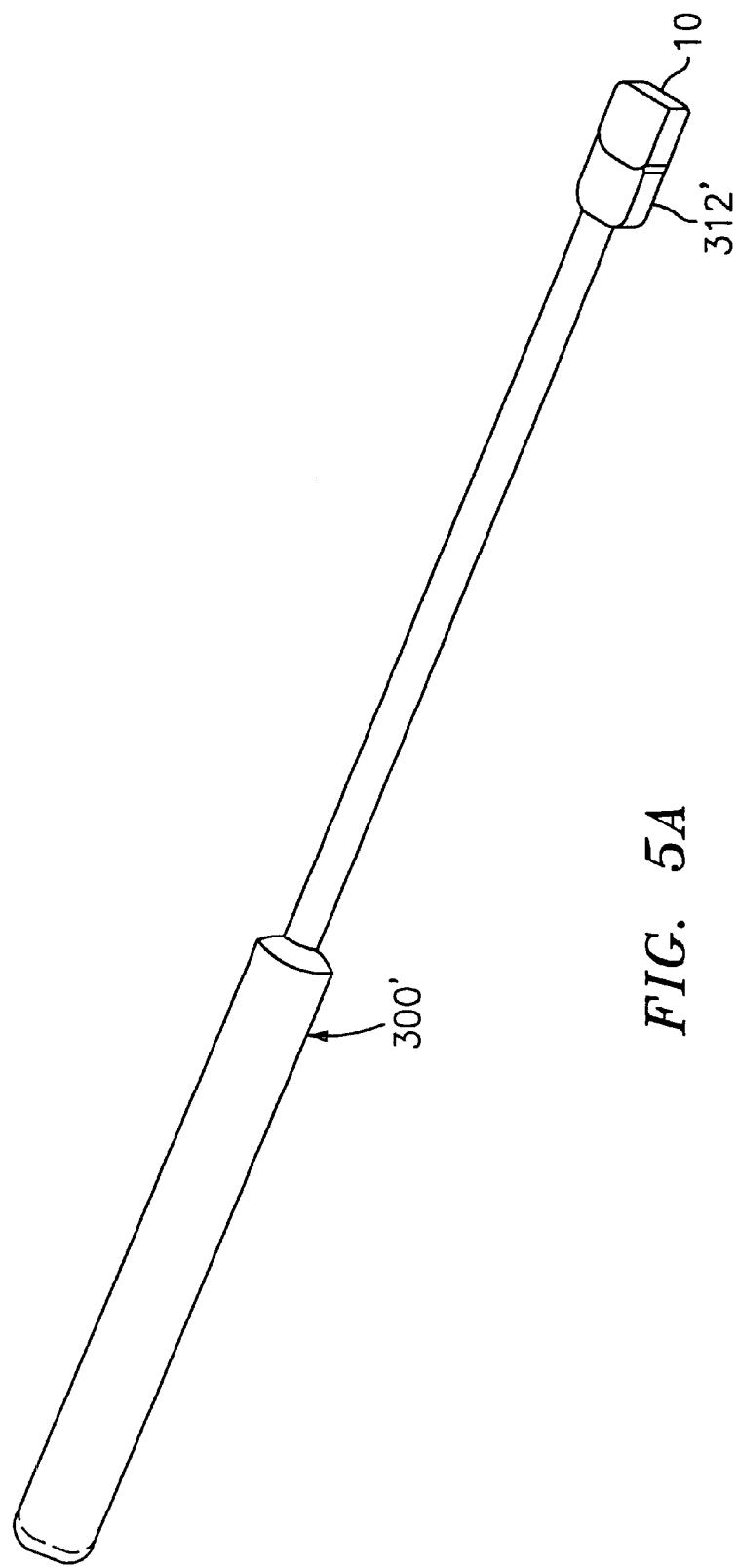
FIG. 5A is a perspective view of an alternate embodiment of the presently disclosed bone tamp.
Figure 5B:
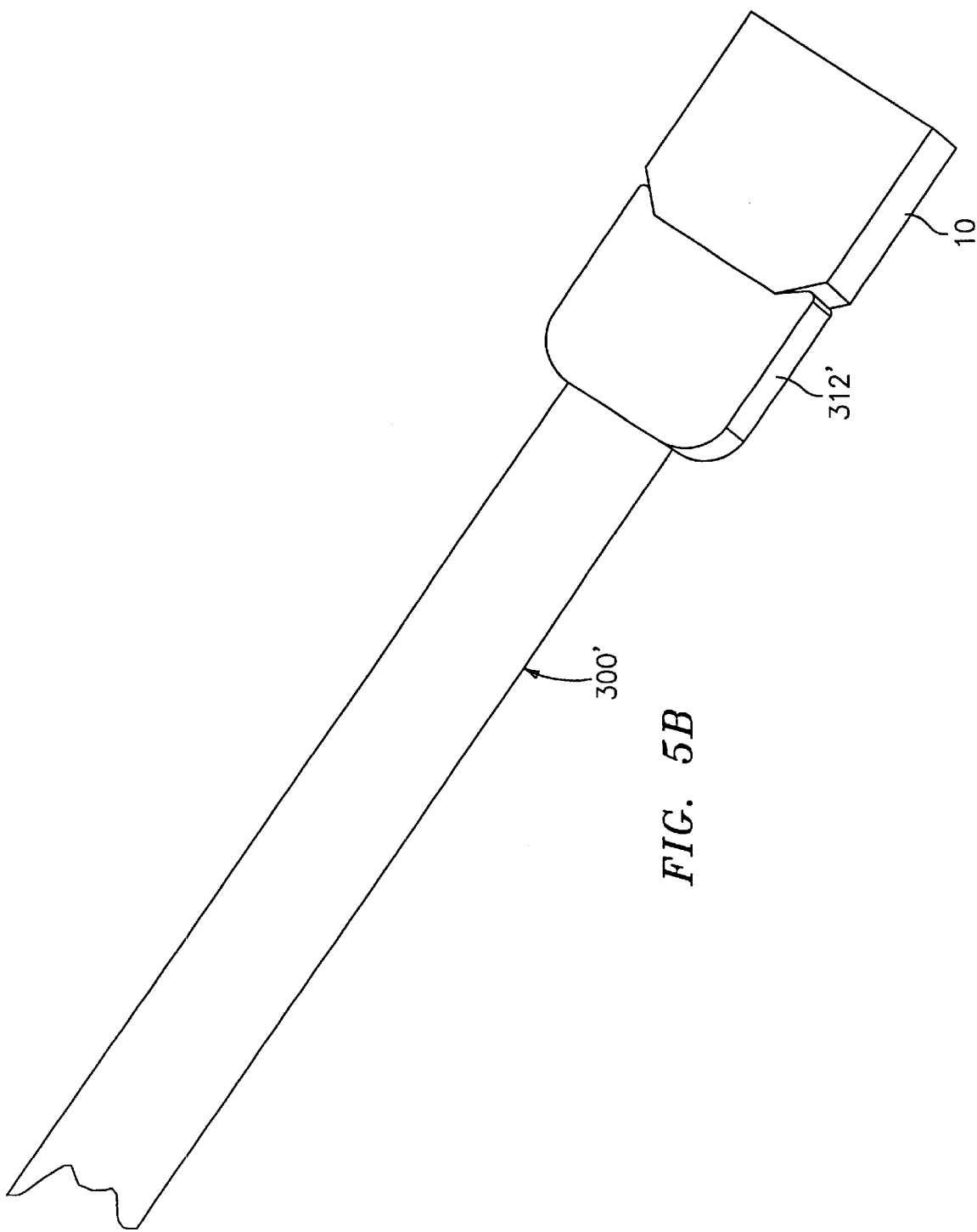
FIG. 5B is a perspective cutaway view of the distal end of the bone tamp shown in FIG. 5A.

Referring to FIG. 5, after a spacer has been partially positioned within a receiving bed, recess 318 of head portion 312 is positioned in engagement with trailing end 20 of spacer 10. Thereafter, an abutment end 324 of handle portion 310 can be tapped with a mallet to drive the spacer into the receiving bed. Insertion is complete when stops 322 engage the adjacent vertebrae. In an alternate embodiment shown in FIGS. 5A and 5B, head portion 312' of bone tamp 300' does not include stops.

Figure 6:
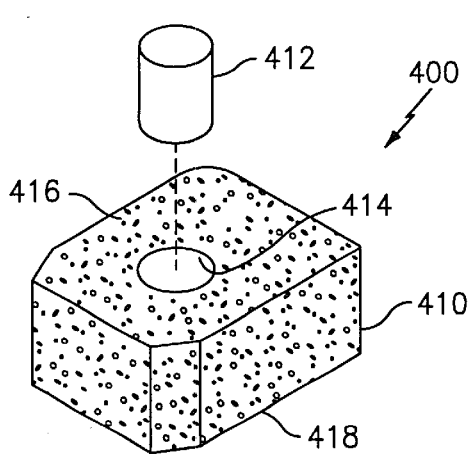
FIG. 6 is a perspective view with parts separated of another preferred embodiment of the presently disclosed intervertebral spacer.
Figure 7:
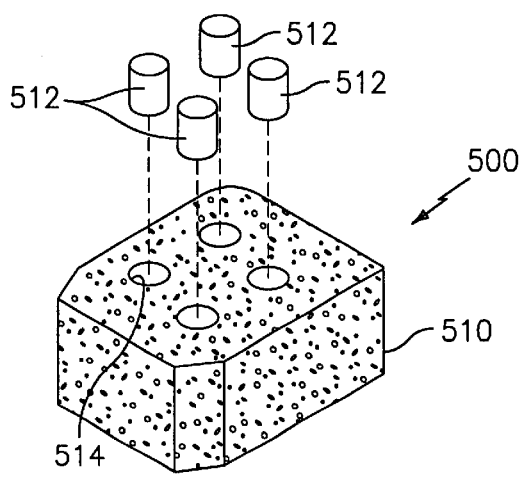
FIG. 7 is a perspective view with parts separated of another preferred embodiment of the presently disclosed intervertebral spacer.

FIG. 6 illustrates an alternate embodiment of the presently disclosed intervertebral spacer which is shown generally as 400. Spacer 400 is similar to spacer 10, but also includes a plug or pillar 412 formed of cortical bone tissue. Pillar 412 is positioned within a bore 414 extending between top and bottom surfaces 416 and 418 of body 410. Although illustrated as being cylindrical in shape, pillar 112 may assume other configurations, e.g., rectangular, hexagonal, square, etc. Alternately, intervertebral spacer may be formed having plurality of spaced pillars. For example, intervertebral spacer 500, shown in FIG. 7 includes four cortical pillars supported within bores 514 extending between top and bottom surfaces 516 and 518 of cancellous body 510. By providing cortical posts in a cancellous body, the spacer has improved strength while maintaining its osteoinductive properties.

Figure 8A:
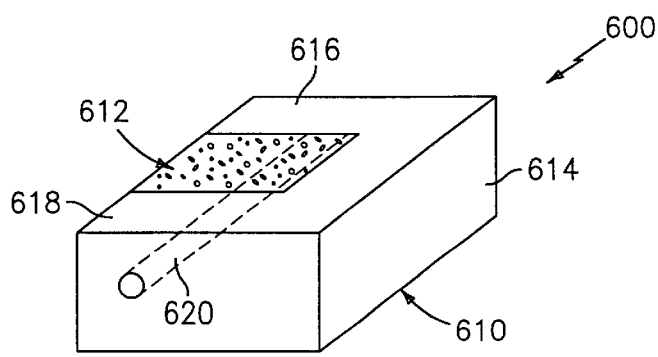
FIG. 8A is a perspective view of yet another embodiment of the presently disclosed intervertebral spacer.

FIG. 8A illustrates another embodiment of the presently disclosed intervertebral spacer shown generally as 600. Spacer 600 has a substantially rectangular shape and includes a U-shaped body portion 610 and a central body portion 612. U-shaped body portion 610 is formed of cortical bone and includes a base 614 and first and second legs 616 and 618. Central body 612 is formed of cancellous bone which is positioned between first and second legs 616 and 618 of U-shaped body portion 610. A retaining pin 620 may be positioned to extend between legs 616 and 618 through body portion 612 to prevent body portion 612 from separating from body portion 610. Retaining pin 620 may be formed of cancellous or cortical bone, or alternately, from any bio-compatible material having the requisite strength requirements including metals, plastics, composites, etc . . .

Figure 8B:
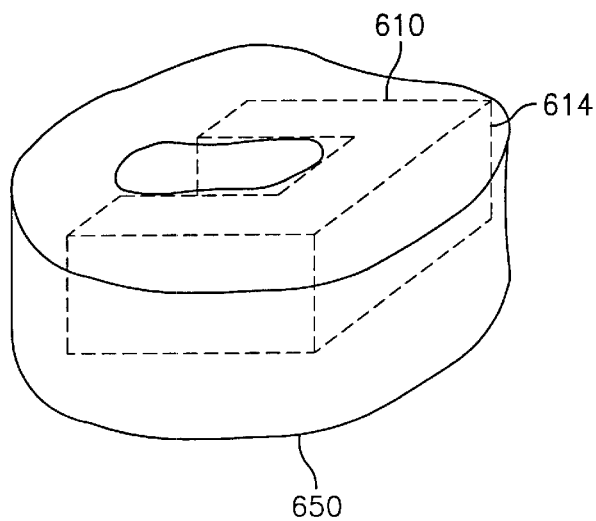
FIG. 8B is a perspective view of a femoral ring from which the intervertebral spacer shown in FIG. 8A can be formed.
Figure 8C:
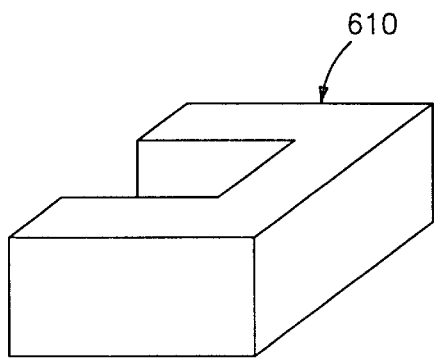
FIG. 8C is a perspective view of the cortical shell of the intervertebral spacer shown in FIG. 8A.

Referring to FIGS. 8B and 8C, cervical spacer 600 can be formed by cutting U-shaped portion 610 from a cortical ring 650 which may be cut from a long bone, e.g., femur, tibia, fibula, ulna or radius. Body portion 610 (FIG. 8A) which is formed from dense cancellous bone, can be inserted thereafter and pinned therein if necessary.

Each of intervertebral spacers 10, 400, 500 and 600 may be formed from partially or fully demineralized bone. The bone may be partially demineralized, e.g., surface demineralized, to provide a degree of flexibility to the spacer or to improve the osteoinductive characteristics of the spacer. Alternately, the spacer may be formed of fully demineralized bone for the same reasons. In one preferred embodiment, the cancellous body of the spacer is formed of partially or fully demineralized bone while the cortical pillars are formed of mineralized bone. By demineralizing the cancellous body an osteoconductive matrix is provided about the cortical pillars to maintain the pillars in their designated spatial relationship. Alternately, any portion of implants 10, 400, 500 and 600 may be partial or fully demineralized to provide the improved characteristics discussed above.

It will be understood that various modifications may be made to the embodiments disclosed herein. For example, the number of cortical pillars may be varied to suit a particular surgical procedure. Moreover, the cortical bone may be replaced with other bio-compatible materials having the requisite strength requirements including ceramics, polymers, composites, etc. BMP's may be added to the material used to construct the intervertebral spacer to promote osteoinductivity. Furthermore, the spacers are not limited to use in the cervical spine, but rather may be suitable for use in the lumbar and/or thoracic spine. Additionally, the intervertebral spacer is not limited to the shape illustrated but rather may be configured to suit a particular procedure, i.e., the spacer may be circular, rectangular, square, etc. The shape of the recess in the bone tamp may also be varied accordingly. Therefor, the above description should not be constructed as limiting, but merely as exemplifications of preferred embodiments. Those skilled in the art will envision other modifications within the scope and spirit of the claims appended hereto.

What is claimed is:

1. An intervertebral spacer for intervertebral implantation, the intervertebral spacer comprising:
   a body formed of dense cancellous bone, the body having a leading end, a trailing end, a planar top surface, a planar bottom surface, and at least one sidewall, and
   a shell formed of cortical bone which is positioned about at least a portion of the body,
   wherein the body has a substantially rectangular configuration and the shell is U-shaped, the shell being positioned in relation to the body about at least a portion of the sidewalls of the body.

2. An intervertebral spacer according to claim 1, wherein the body has a substantially rectangular configuration.

3. An intervertebral spacer according to claim 2 further comprising a pair of angled sidewalls, one of the angled sidewalls being positioned on each end of the trailing end and each angled sidewall connecting the trailing end with the at least one sidewall.

4. An intervertebral spacer according to claim 1, further including at least one post formed of cortical bone, the at least one post extending between the top and bottom surfaces of the body.

5. An intervertebral spacer according to claim 4, wherein the post is cylindrical.

6. An intervertebral spacer according to claim 4, wherein the at least one post includes a plurality of posts formed of cortical bone.

7. An intervertebral spacer according to claim 6, wherein four of said posts are positioned in spaced relation within the matrix.

8. An intervertebral spacer according to claim 6, wherein the plurality of posts includes four posts supported in spaced relation within the body.

9. An intervertebral spacer according to claim 6, further including at least one post formed of a load bearing bio-compatible material.

10. An intervertebral spacer according to claim 9, wherein the at least one post includes a plurality of posts.

11. An intervertebral spacer according to claim 9, wherein the biocompatible material is selected from the group consisting of polymers, ceramics and metals.

* * * * *